(12) United States Patent
Ellegala

(10) Patent No.: US 12,156,645 B2
(45) Date of Patent: Dec. 3, 2024

(54) MODIFIED ULTRASOUND ASPIRATOR FOR USE IN AND AROUND VITAL STRUCTURES OF A BODY

(71) Applicant: Dilantha B. Ellegala, Lynchburg, VA (US)

(72) Inventor: Dilantha B. Ellegala, Lynchburg, VA (US)

(*) Notice: Subject to any disclaimer, the term of this patent is extended or adjusted under 35 U.S.C. 154(b) by 231 days.

(21) Appl. No.: 17/245,819

(22) Filed: Apr. 30, 2021

(65) Prior Publication Data

US 2021/0290260 A1    Sep. 23, 2021

Related U.S. Application Data

(63) Continuation of application No. 15/305,738, filed as application No. PCT/US2015/027531 on Apr. 24, 2015, now abandoned.

(Continued)

(51) Int. Cl.
*A61B 17/02* (2006.01)
*A61B 1/015* (2006.01)
(Continued)

(52) U.S. Cl.
CPC .......... *A61B 17/0218* (2013.01); *A61B 1/015* (2013.01); *A61B 1/018* (2013.01); *A61B 17/00234* (2013.01); *A61B 17/320092* (2013.01); *A61B 90/06* (2016.02); *A61B 90/08* (2016.02); *A61B 90/30* (2016.02); *A61M 3/0283* (2013.01); *A61B 2017/00022* (2013.01); *A61B 2017/00039* (2013.01); *A61B 2017/00057* (2013.01); *A61B 2017/00106* (2013.01); *A61B 2017/00115* (2013.01); *A61B 2017/00296* (2013.01); *A61B 2017/00336* (2013.01);
(Continued)

(58) Field of Classification Search
CPC .......... A61B 17/0218; A61B 17/00234; A61B 17/320092; A61B 2017/00115; A61B 2017/00336; A61B 90/06; A61B 90/08; A61B 90/30; A61B 1/018; A61M 1/0039; A61M 1/0058; A61M 1/008; A61M 1/0084
See application file for complete search history.

(56) References Cited

U.S. PATENT DOCUMENTS 3,805,787 A    4/1974    Kresch et al.
4,417,578 A    11/1983   Banko
(Continued)

FOREIGN PATENT DOCUMENTS

WO    97/36546 A1    10/1997

OTHER PUBLICATIONS

Communication dated Dec. 4, 2017, from European Patent Office in counterpart application No. 15782892.2.
(Continued)

*Primary Examiner* — Ashley L Fishback
(74) *Attorney, Agent, or Firm* — Sughrue Mion, PLLC

(57) ABSTRACT

An ultrasonic aspirator includes a body, an aspirator wand extending from the body, a shield to cover the aspirator wand, a removable headpiece removably attached to the aspirator wand, and a guard extending past an end of the headpiece in a direction distal to the body, the aspirator also includes a generator or a detector to generate or detect electrical pulses, light sources, endoscopy, modified body angles, image navigation integration for improved visualization and optimization of the surgical field.

20 Claims, 21 Drawing Sheets

Related U.S. Application Data

(60) Provisional application No. 62/114,824, filed on Feb. 11, 2015, provisional application No. 62/028,044, filed on Jul. 23, 2014, provisional application No. 61/983,759, filed on Apr. 24, 2014.

(51) Int. Cl.
| | |
|---|---|
| *A61B 1/018* | (2006.01) |
| *A61B 17/00* | (2006.01) |
| *A61B 17/32* | (2006.01) |
| *A61B 90/00* | (2016.01) |
| *A61B 90/30* | (2016.01) |
| *A61M 3/02* | (2006.01) |

(52) U.S. Cl.
CPC ............... *A61B 2017/00738* (2013.01); *A61B 2017/32007* (2017.08); *A61B 2017/320075* (2017.08); *A61B 2017/320084* (2013.01); *A61B 2090/061* (2016.02); *A61B 2090/063* (2016.02); *A61B 2090/065* (2016.02); *A61B 2090/08021* (2016.02)

(56) References Cited

U.S. PATENT DOCUMENTS

| | | | |
|---|---|---|---|
| 5,058,570 A | 10/1991 | Idemoto et al. | |
| 5,123,903 A | 6/1992 | Quaid et al. | |
| 5,456,689 A | 10/1995 | Kresch et al. | |
| 6,013,046 A | 1/2000 | Maaskamp et al. | |
| 6,270,471 B1 | 8/2001 | Hechel | |
| 6,340,352 B1 | 1/2002 | Okada et al. | |
| 6,524,251 B2 | 2/2003 | Rabiner et al. | |
| 7,942,834 B2 | 5/2011 | Yamada et al. | |
| 8,376,970 B2 | 2/2013 | Babaev | |
| 8,435,259 B2 | 5/2013 | Dierck | |
| 8,469,981 B2 | 6/2013 | Robertson | |
| 8,512,340 B2 | 8/2013 | Easley et al. | |
| 8,591,536 B2 | 11/2013 | Robertson | |
| 8,632,561 B2 | 1/2014 | Siepel et al. | |
| 8,663,227 B2 | 3/2014 | To | |
| 2005/0096649 A1 | 5/2005 | Adams | |
| 2005/0177184 A1 | 8/2005 | Easley | |
| 2006/0241580 A1 | 10/2006 | Mittelstein et al. | |
| 2008/0249404 A1 | 10/2008 | Mikkaichi et al. | |
| 2008/0281267 A1 | 11/2008 | Mehier | |
| 2009/0018490 A1 | 1/2009 | Wuchinich | |
| 2009/0124975 A1 | 5/2009 | Oliver et al. | |
| 2009/0192441 A1 | 7/2009 | Gelbart et al. | |
| 2009/0270791 A1 | 10/2009 | Todd et al. | |
| 2012/0259317 A1 | 10/2012 | Baldwin et al. | |
| 2014/0058427 A1 | 2/2014 | Robertson | |
| 2014/0074013 A1 | 3/2014 | McCary et al. | |

OTHER PUBLICATIONS

Communication dated Mar. 12, 2018, from European Patent Office in counterpart application No. 15782892.2.
International Search Report of PCT/US2015/027531 dated Sep. 15, 2015 [PCT/ISA/210].
Written Opinion of PCT/US2015/027531 dated Sep. 15, 2015 [PCT/ISA/237].

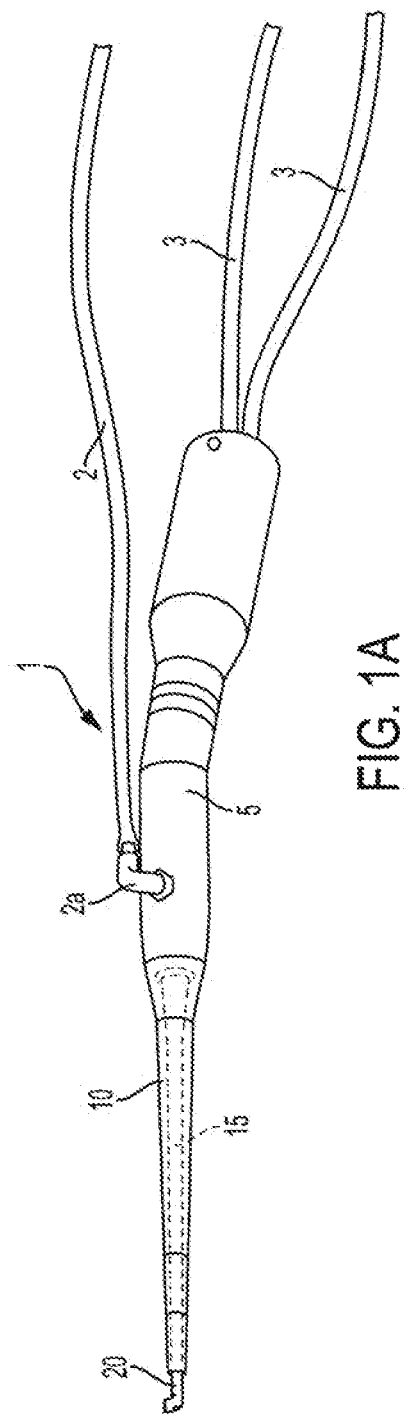
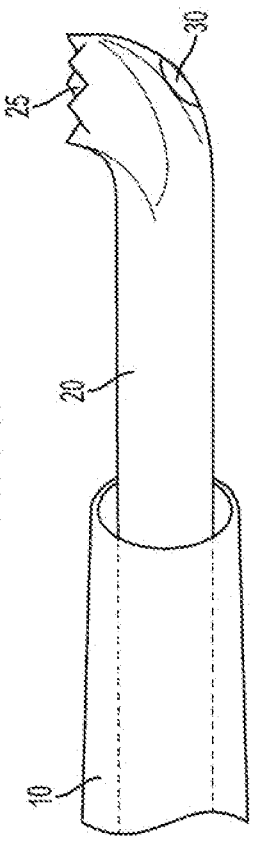
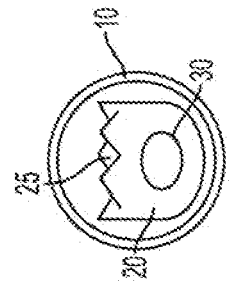
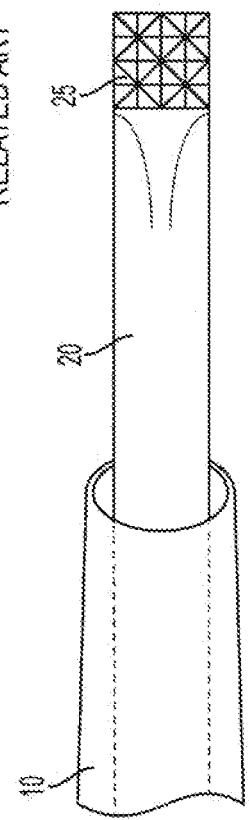
FIG. 1A RELATED ART
FIG. 1B RELATED ART
FIG. 1D RELATED ART
FIG. 1C RELATED ART

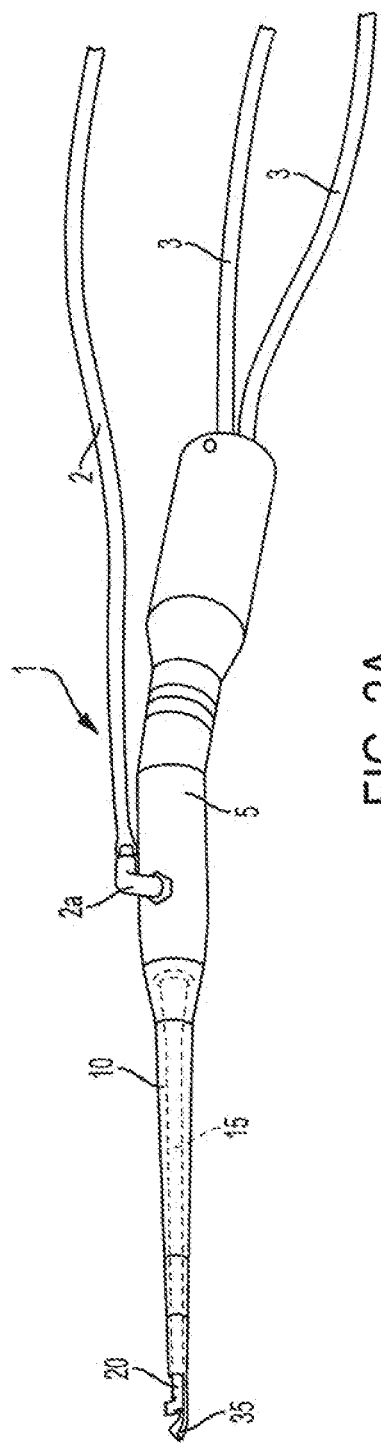
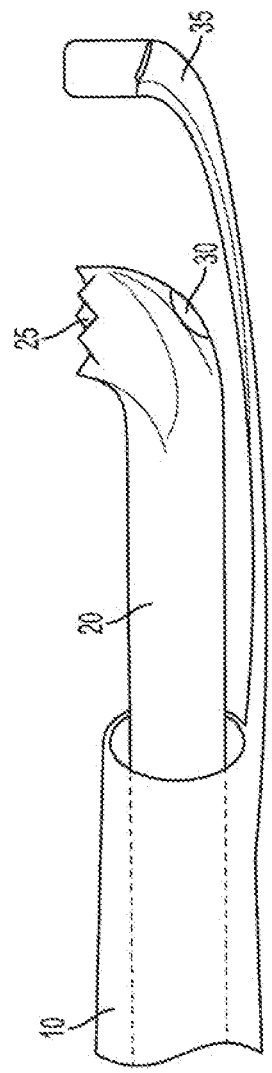
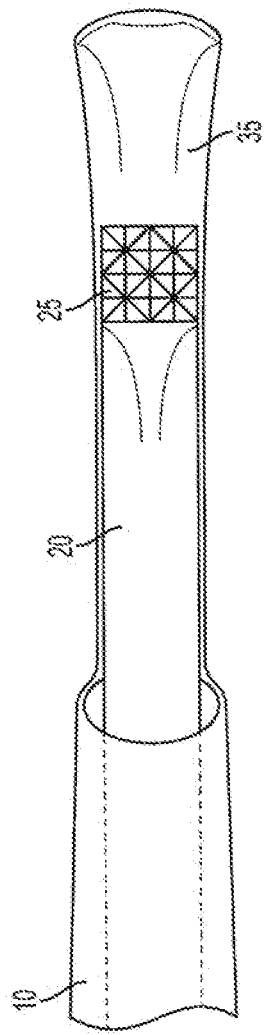
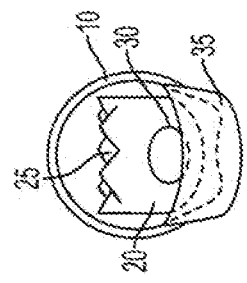
FIG. 2A
FIG. 2B
FIG. 2C
FIG. 2D

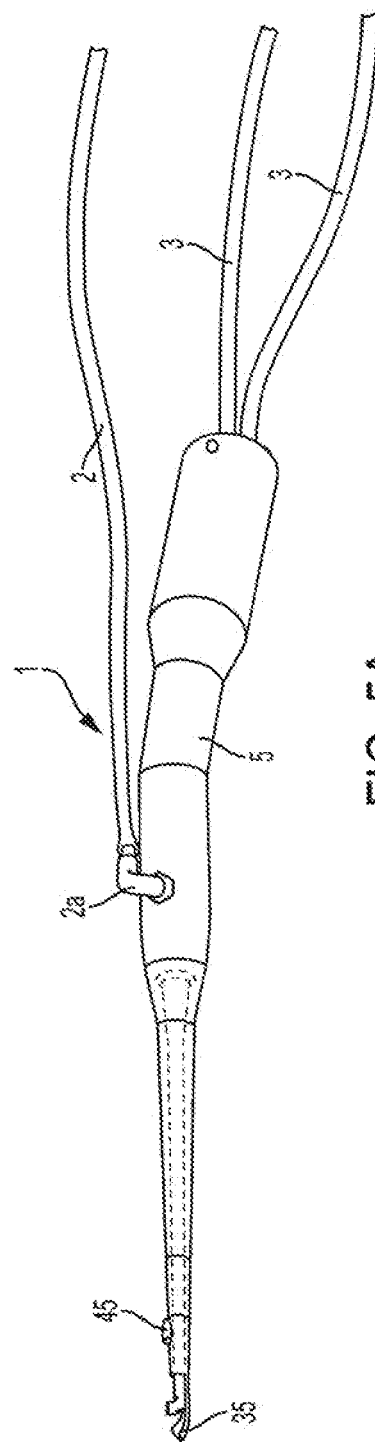
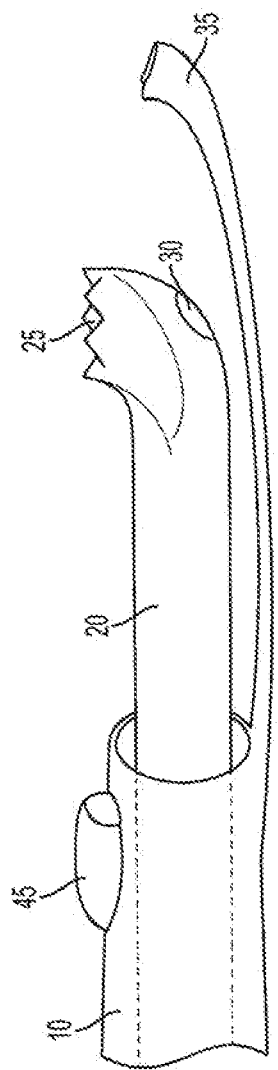
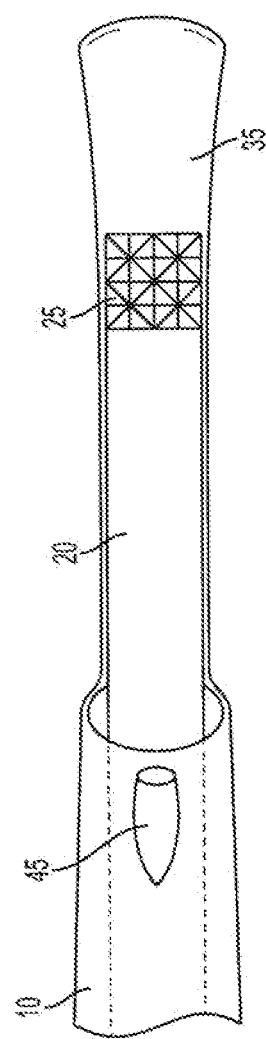
FIG. 5A
FIG. 5B
FIG. 5C

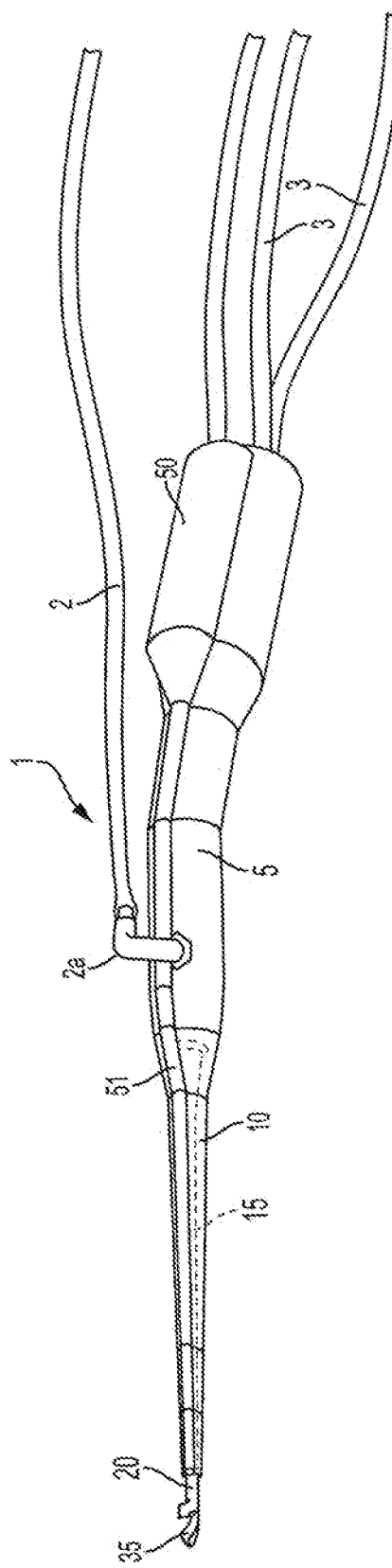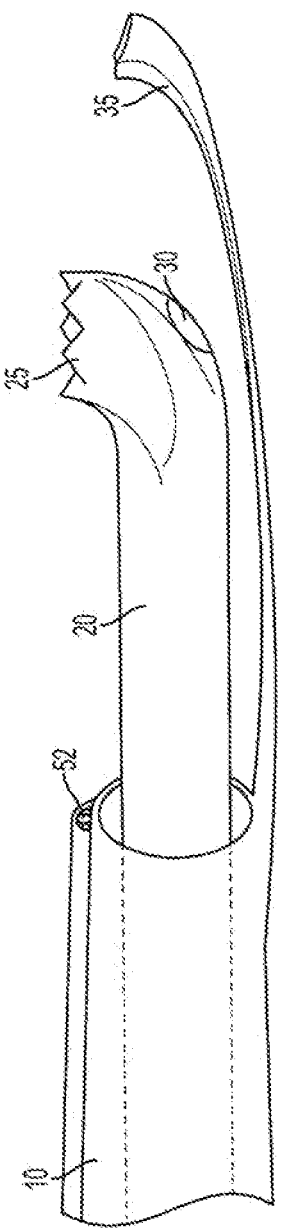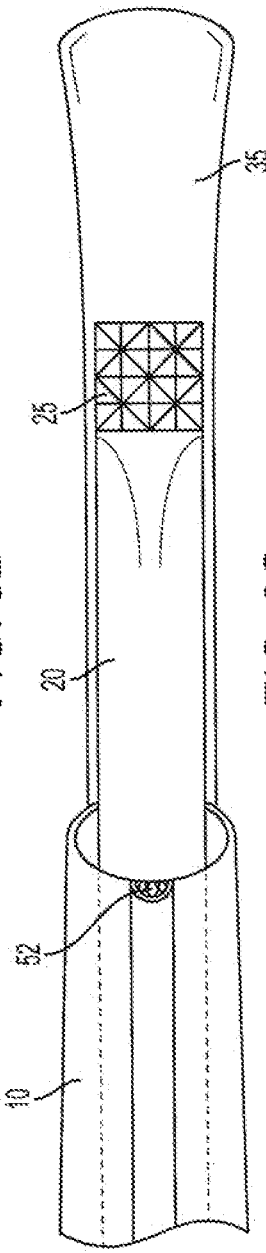
FIG. 6A
FIG. 6B
FIG. 6C

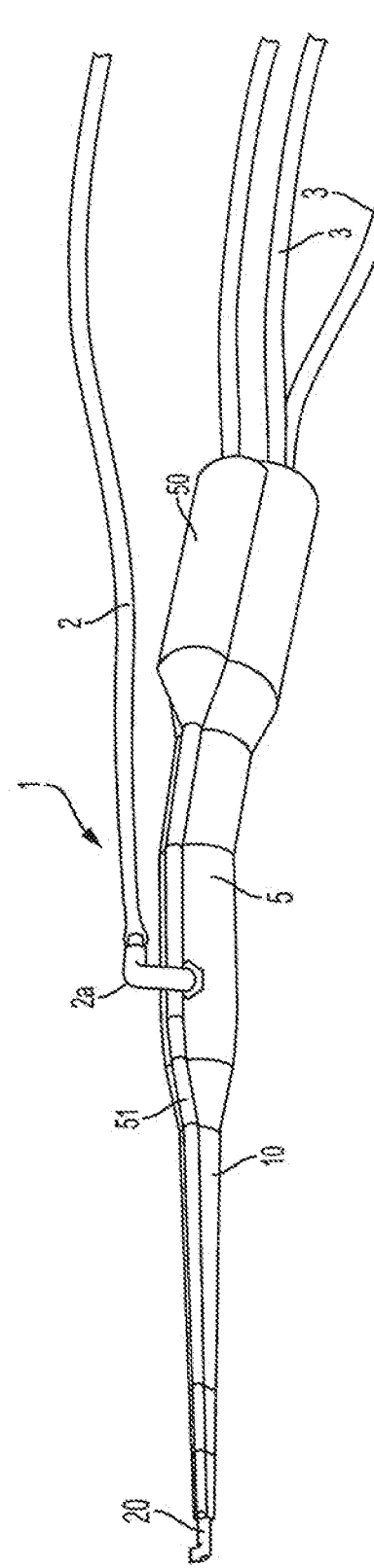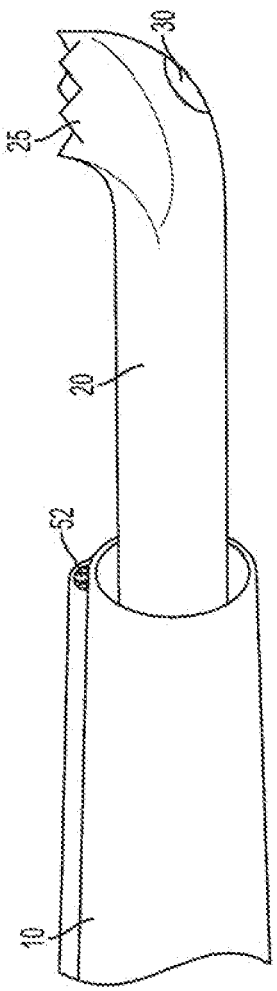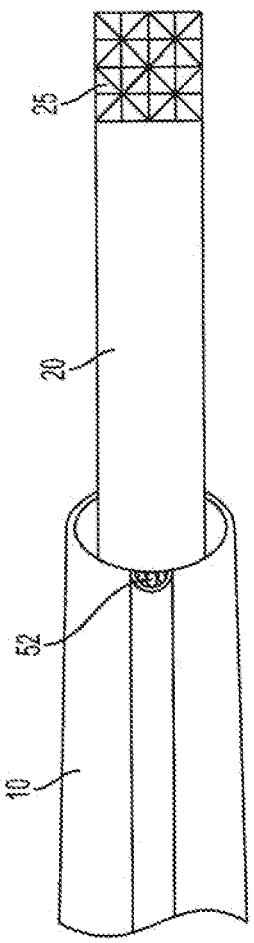

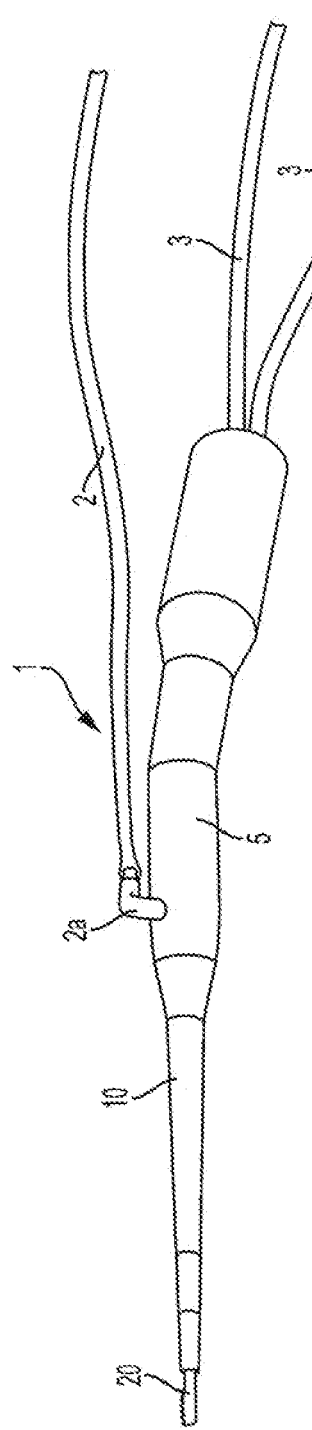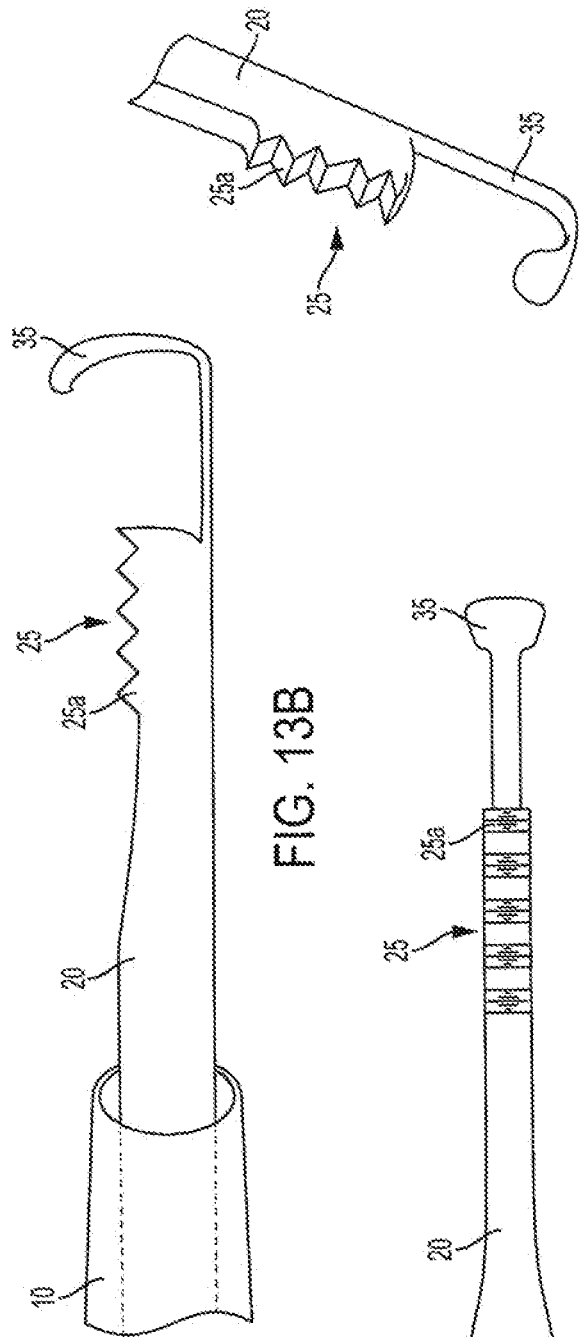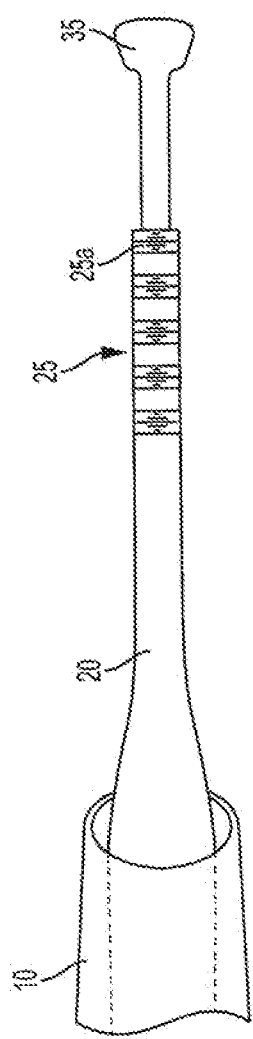
FIG. 13A
FIG. 13B
FIG. 13C
FIG. 13D

MODIFIED ULTRASOUND ASPIRATOR FOR USE IN AND AROUND VITAL STRUCTURES OF A BODY

CROSS-REFERENCE TO RELATED APPLICATION

This is a Continuation application of U.S. National Stage Application Ser. No. 15/305,738 filed on Oct. 21, 2016, which claims priority from U.S. Provisional Application No. 61/983,759 filed Apr. 24, 2014, U.S. Provisional Application No. 62/028,044 filed Jul. 23, 2014, and U.S. Provisional Application No. 62/114,824 filed Feb. 11, 2015, the disclosures of which are incorporated herein by reference.

BACKGROUND

1. Field

Exemplary embodiments relate to an ultrasonic aspirator, and more particularly, to an ultrasonic aspirator that enables safer and expanded use around vital structures of a body.

2. Description of the Related Art

In recent years, brain and spine surgery has progressed to include minimally invasive procedures, which reduces a patient's hospital stay and reduces recovery time, which has led to an overall reduction in costs. However, the use of minimally invasive procedures requires that standard operating room tools be modified to complete these tasks.

There presently exists ultrasonic aspirators for use in removing tissue in the human body. These conventional ultrasonic aspirators use ultrasound energy transmitted along a length of metal to cause a vibration of the metal and destruction of the tissue. The ultrasonic aspirator also integrates suction and irrigation to reduce thermal injury to tissue adjacent to the target area by the heating of the metal tip. Due to the bulk of the apparatuses and the lack of visualization associated of the conventional technology, the conventional technology is unsuitable for use in minimally invasive surgeries.

Accordingly, an ultrasound tissue aspirator is needed for use around sensitive and easily damaged tissue, including nerves and brain matter, by minimizing thermal injury to the tissue and by minimizing or eliminating the unintended destructive effects of the ultrasound itself.

In addition, the need to integrate a light sources, nerve stimulators/monitors, endoscopes, and navigation probes, to further enhance the safety of ultrasound tissue aspirators in small working spaces with poor visibility is required. Moreover, exemplary embodiments integrate various tools with an ultrasound aspirator to reduce the need to change devices in a fixed, closed space, thereby reducing the operating time.

SUMMARY

It is an aspect of the exemplary embodiments to provide a guard for an ultrasonic aspirator to prevent the unintentional destruction of tissue around a targeted aspiration area. Further, it is an aspect of the exemplary embodiments to provide an endoscope and/or a light to provide better visualization of a targeted surgical area.

An ultrasonic aspirator according to an exemplary embodiment includes a body, an aspirator wand extending from the body, a shield to cover the aspirator wand, a removable headpiece removably attached to the aspirator wand, and a guard extending past an end of the headpiece in a direction distal to the body.

According to an exemplary embodiment, the guard is attached to the shield.

According to an exemplary embodiment, the guard is attached to the body.

According to an exemplary embodiment, the guard is integral with the headpiece.

According to an exemplary embodiment, the guard is separated from the headpiece by a material that is non-conductive of heat or vibration.

According to an exemplary embodiment, the ultrasonic aspirator further includes a light integrally formed at an end of the shield in a direction distal to the body.

According to an exemplary embodiment, the ultrasonic aspirator further includes an endoscope integrally formed with the body and the shield, extending from the body to an end of the shield in a direction distal to the body.

According to an exemplary embodiment, a first side of the headpiece includes a working surface to aspirate an object, and the first side of the headpiece further includes a suction opening in a direction proximal to the body from the headpiece.

According to an exemplary embodiment, the ultrasonic aspirator further includes a hollow tube extending from the body through the shield and terminating at the suction opening.

According to an exemplary embodiment, the headpiece includes a working surface having a plurality of protrusions to cut the object.

According to an exemplary embodiment, the headpiece includes a working surface being having a width greater than a width of the headpiece.

According to an exemplary embodiment, the headpiece includes at least one joint around which a working surface of the headpiece can bend.

According to an exemplary embodiment, the headpiece includes a sensor receives an input from an adjacent object.

According to an exemplary embodiment, the sensor receives as input a vibration of the adjacent object.

According to an exemplary embodiment, the headpiece includes a grasper at the end of the headpiece distal to the body.

An ultrasonic aspirator/sonicator according to an exemplary embodiment includes a body, an aspirator wand extending from the body, a shield to cover the aspirator wand, a removable headpiece removably attached to the aspirator wand, and a sensor to determine a change in a density of an object contacted by the headpiece, where the aspirator is stopped when the sensor determines that the density of the object has changed.

According to an exemplary embodiment, the sensor is a pressure sensor.

According to an exemplary embodiment, the sensor is an ultrasonic sensor.

According to an exemplary embodiment, the sensor is a displacement sensor.

According to an exemplary embodiment, the sensor tip is integrated into image navigation.

An ultrasonic aspirator/sonicator according to an exemplary embodiment includes a body, an aspirator wand extending from the body, a shield to cover the aspirator wand, and a removable headpiece removably attached to the aspirator wand, where at least part of the headpiece is bends according to a user's input.

BRIEF DESCRIPTION OF THE DRAWINGS

These and/or other aspects will become apparent and more readily appreciated from the following description of exemplary embodiments, taken in conjunction with the accompanying drawings of which:

FIGS. 1A-ID are views showing a conventional ultrasound aspirator;

FIGS. 2A-2D are views showing an ultrasound aspirator having a guard attached to a shield of the ultrasound aspirator according to an exemplary embodiment;

FIGS. 5A-5C are views showing an ultrasound aspirator having an integrated light according to an exemplary embodiment;

FIGS. 6A-6C are views showing an ultrasound aspirator having an integrated guard and endoscope according to an exemplary embodiment;

FIGS. 9A-9C are views showing an ultrasound aspirator having an integrated endoscope only according to an exemplary embodiment;

FIGS. 13A-13D are views showing an ultrasound aspirator/sonicator having a specialty cutting blade on the headpiece and a guard integrally formed with the headpiece according to an exemplary embodiment;

FIGS. 14A-14I) are views showing an ultrasound aspirator/sonicator having a specialty cutting blade on the headpiece and a guard integrally formed with the shield according to an exemplary embodiment;

DETAILED DESCRIPTION

Figure 3A:
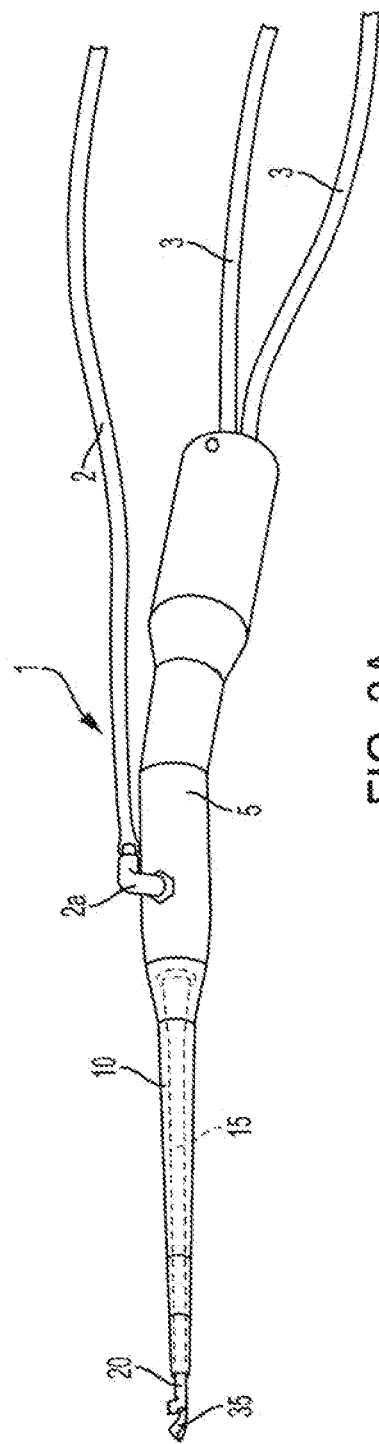
FIGS. 3A-3C are views showing an ultrasound aspirator having a guard integrally formed with a headpiece of the ultrasound aspirator according to an exemplary embodiment.

Reference will now be made in detail to exemplary embodiments, examples of which are illustrated in the accompanying drawings, wherein like reference numerals refer to like elements throughout. However, known functions associated with the exemplary embodiments or detailed descriptions on the configuration and other matters which would unnecessarily obscure the present disclosure will be omitted.

FIGS. 1A-1D are views showing a conventional ultrasonic aspirator 1. The ultrasonic aspirator 1 is used to remove tissue from a body, such as a human body or an animal body. Ultrasound energy is transmitted from the body 5 of the ultrasound aspirator 1, down an aspirator wand 15, and to the removable headpiece 20. The ultrasound energy causes the headpiece 20 to vibrate and destroy tissue. As shown in FIG. 1A, an irrigation hose 2 can provide fluid to the body 5, through the irrigation port 2a, provide the fluid to the headpiece 20 to aid in the removal of destroyed tissue and reduce thermal injury to adjacent tissue caused by the heating of the headpiece 20. The ultrasound aspirator is powered by power cables 3.

As shown in FIGS. 1A-ID, the ultrasonic aspirator 1 further includes a shield 10 to carry fluid for aspiration of sonicated tissue and prevent contact of the aspirator wand 15 with tissue or other objects. Referring to FIGS. 1B and 1D, there is provided a suction opening 30 at a distal, tip end of the headpiece 20. The suction opening 30 can be used to remove liquid, tissue, and other debris in the body during use of the ultrasonic aspirator 1. The headpiece 20 includes a working surface 25. The working surface 25 contacts the tissue or other objects and destroys the tissue or objects by vibrating the working surface 25.

However, tissue and other objects surrounding the targeted tissue may be unintentionally destroyed by the working surface 25 the ultrasonic aspirator 1. That is, the working areas in which the ultrasonic aspirator 1 is used are very small, and the headpiece 20 and working surface 25 is used may unintentionally contact tissue or other objects adjacent to the targeted structures. Accordingly, exemplary embodiments are provided to prevent the unintentional contact between the headpiece 20 and working surface 25 of the ultrasonic aspirator 1 and untargeted tissue or other objects.

FIGS. 2A-2D show an ultrasonic aspirator 1 according to an exemplary embodiment. The ultrasonic aspirator 1 according an exemplary embodiment includes a body 5, an irrigation tube 2 connected to the body 5 via an irrigation port 2a, an aspirator wand 15 extending from the body 5, and a headpiece 20 having a working surface 25. Further, the ultrasonic aspirator 1 includes a guard 35. As shown in FIG. 2B, the guard 35 extends past the headpiece 20 in a direction distal to the working surface 25 and a distal end of the guard curves around a distal end of the headpiece past a central axis of the headpiece. The distance between the distal end of the working surface 25 and the guard 35 may vary depending on the procedure being performed.

According to an exemplary embodiment, the guard 35 extends from the shield 10, where a space exists between the guard 35 and the headpiece 20 and working surface 25.

The shield 10 may be formed of a plastic, a metal alloy, or any other material that does not conduct heat or ultrasonic vibrations or dampen ultrasonic vibrations. The guard 35 may also be formed of a plastic a metal alloy, or any other material that does not conduct heat or ultrasonic vibrations. The headpiece 20 and the working surface 25 may be formed of any metal or other material that conducts heat and ultrasonic vibrations. It will be understood by those skilled in the art that these materials am only exemplary, and any material suitable for the intended purpose of the structure may be used.

Figure 3B:
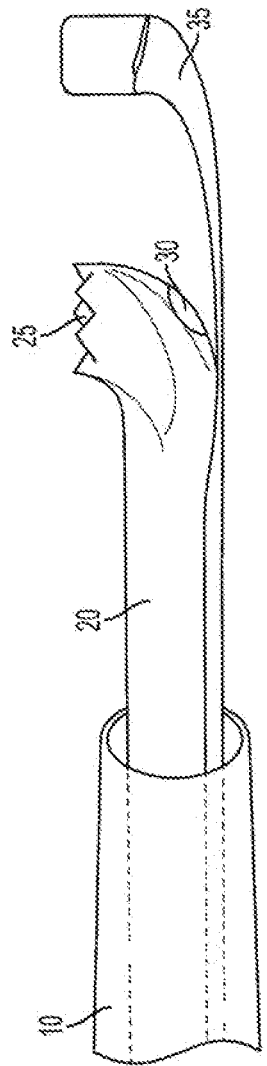
Figure 3C:
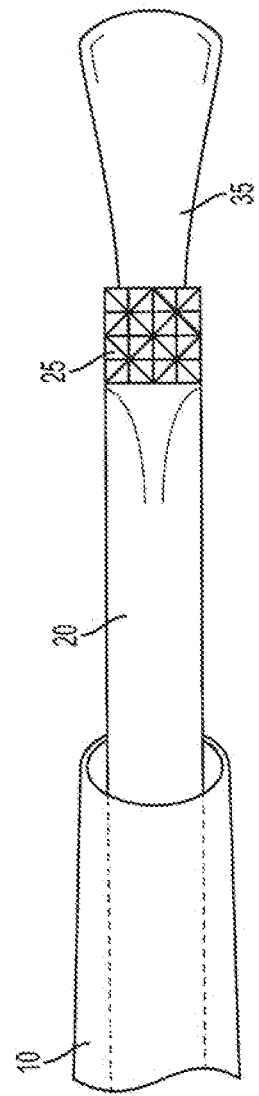

Referring to FIGS. 3A-3D, an ultrasonic aspirator 1 according to an exemplary embodiment is shown. The ultrasonic aspirator 1 includes a body 5, an irrigation tube 2 connected to the body 5 via an irrigation port 2a, an aspirator wand 15 extending from the body 5, and a headpiece 20 having a working surface 25. As shown in FIG. 3B, a guard 35 is integrally formed with the headpiece 20 and extends past the headpiece 20 in a direction distal to the body 5. The guard 35 is formed of a material that does not conduct heat or a vibration. Thus, the guard 35 protects tissue surrounding the targeted tissue from being unintentionally destroyed while using the ultrasonic aspirator 1.

Figure 4A:
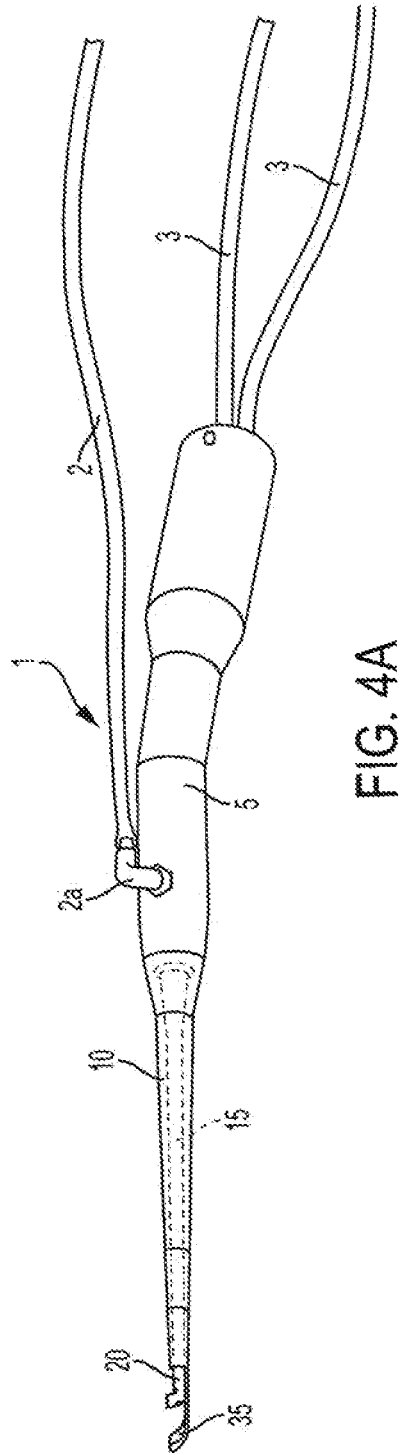
FIGS. 4A-4C are views showing an ultrasound aspirator having a guard attached to a shield and connected to the headpiece of the ultrasound aspirator by a non-conductive material according to an exemplary embodiment.
Figure 4B:
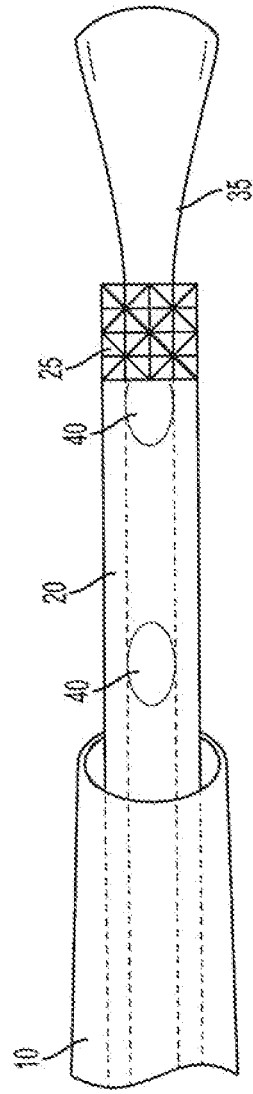
Figure 4C:
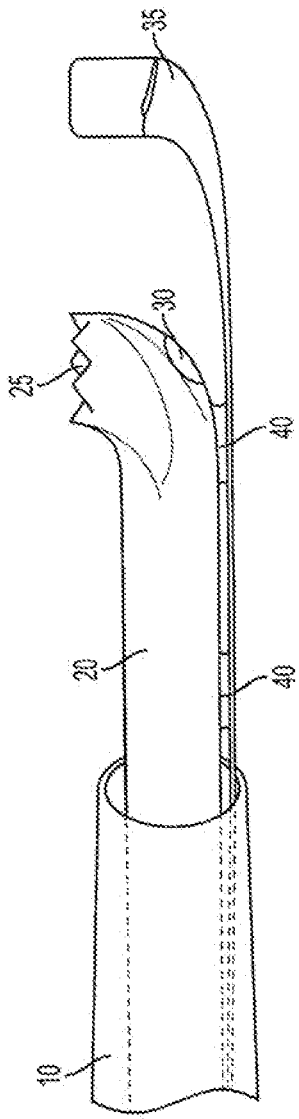

Referring to FIGS. 4A-4C, there is shown an ultrasonic aspirator 1 according to an exemplary embodiment. The ultrasonic aspirator 1 includes a body 5, an irrigation tube 2 connected to the body 5 via an irrigation port 2a, an aspirator wand 15 extending from the body 5, and a headpiece 20 having a working surface 25. As shown in FIG. 4B, a guard 35 is separated from the headpiece 20 by a non-conducting material 40 that does not conduct heat or ultrasonic vibrations. The non-conducting material 40 may be a plastic, an alloy, or any other material that does not conduct heat or ultrasonic vibrations. Further, the guard 35 extends past the headpiece 20 in a direction distal to the body 5 and a distal end of the guard curves around a distal end of the headpiece. Thus, the guard 35 protects tissue surrounding the targeted tissue from being unintentionally destroyed while using the ultrasonic aspirator 1.

Referring to FIG. 5B, there is shown a light 45 integrally formed with the shield 10. However, it will be understood that the light 45 is not limited to being integrally formed with the shield 10. The light 45 may be provided at any location on the ultrasonic aspirator 1 to provide a user with a good visualization of the area that is targeted by the user. In this manner, a safety of the ultrasonic aspirator will be improved.

The light 45 may be powered by a battery or may be connected to a constant power supply by an electrical cord. However, the light 45 is not limited to being powered in this manner, and may be powered by any means known in the art.

Referring to FIGS. 5A-5C, there is shown an ultrasonic aspirator 1 according to an exemplary embodiment. The ultrasonic aspirator 1 according an exemplary embodiment includes a body 5, an irrigation tube 2 connected to the body 5 via an irrigation port 2a, an aspirator wand 15 extending from the body 5, and a headpiece 20 having a working surface 25. Further, the ultrasonic aspirator 1 includes a guard 35 attached to the shield 10 and a distal end of the guard curves around a distal end of the headpiece past a central axis of the headpiece. However, the guard 35 is not limited to being connected to the shield 10.

Referring to FIG. 6A, there is shown an endoscope 50 located at an end of the body 5. Further, the ultrasonic aspirator 1 includes an endoscope tube 52 extending toward the headpiece 20 and terminating at the endoscope opening 53, as shown in FIGS. 6B and 6C, which is at a location proximal of the headpiece 20 to the body 5.

Referring to FIGS. 6B and 6C, the endoscope opening 52 is integrally formed with the shield 10. However, it will be understood that the endoscope opening 52 is not limited to being integrally formed with the shield 10. The endoscope opening 52 may be provided at any location on the ultrasonic aspirator 1 to provide a user with a good visualization of the area that is targeted by the user. In this manner, a safety of the ultrasonic aspirator will be improved.

Figure 7A:
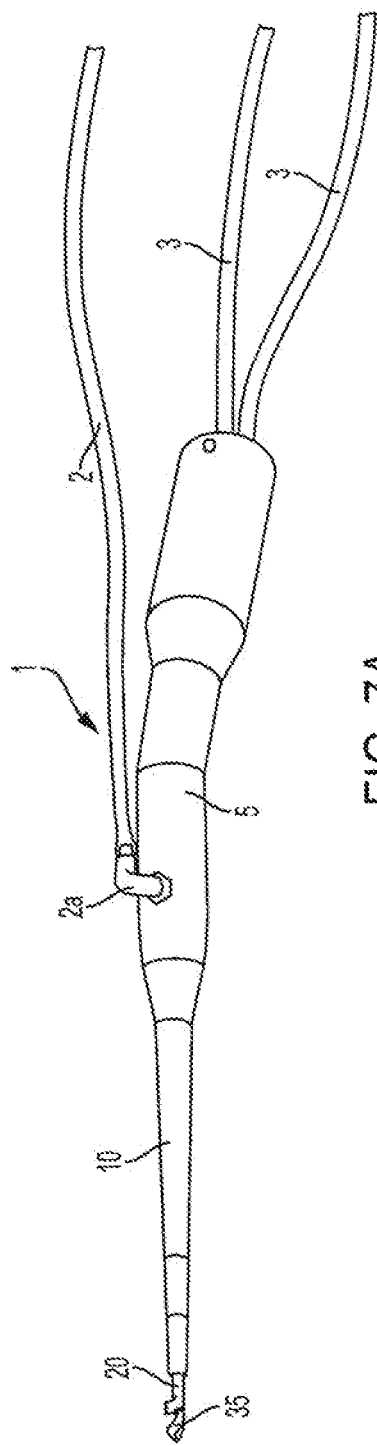
FIGS. 7A-7C are views showing an ultrasonic aspirator having a guard integrally formed with the headpiece of the ultrasound aspirator showing an enhanced suction opening at a distal end of the headpiece according to an exemplary embodiment.
Figure 7B:
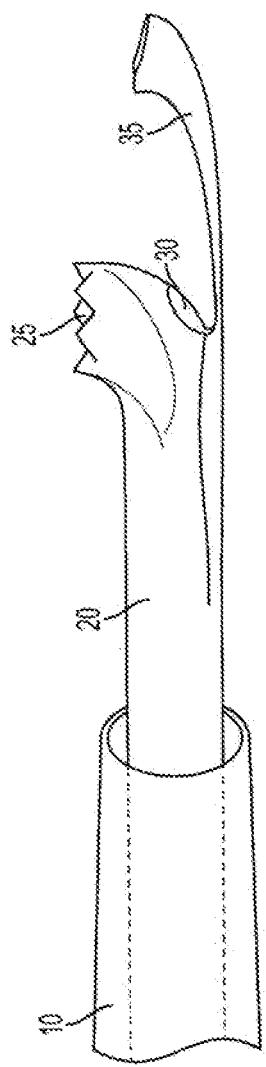
Figure 7C:
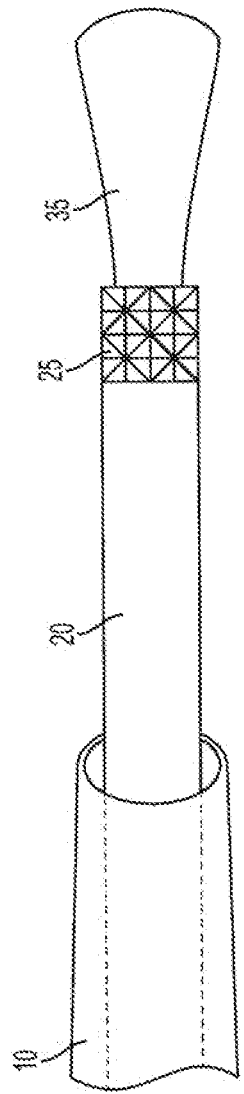

Referring to FIGS. 7A-7C, an ultrasonic aspirator 1 according to an exemplary embodiment is shown. The ultrasonic aspirator 1 includes a body 5, an irrigation tube 2 connected to the body 5 via an irrigation port 2a, an aspirator wand 15 extending from the body 5, and a headpiece 20 having a working surface 25. As shown in FIGS. 7B and 7C, a guard 35 is integrally formed with the headpiece 20 and extends past the headpiece 20 in a direction distal to the body 5.

As shown in FIGS. 7B and 7C, there is provided a suction opening 30 at a distal end of the headpiece 20. The suction opening 30 can be used to remove liquid, tissue, and other debris in the body during use of the ultrasonic aspirator 1. In this manner, the guard 35 protects tissue surrounding the targeted tissue from being unintentionally destroyed while using the ultrasonic aspirator 1, while debris generated during the procedure may be aspirated using the suction opening 30.

Figure 8A:
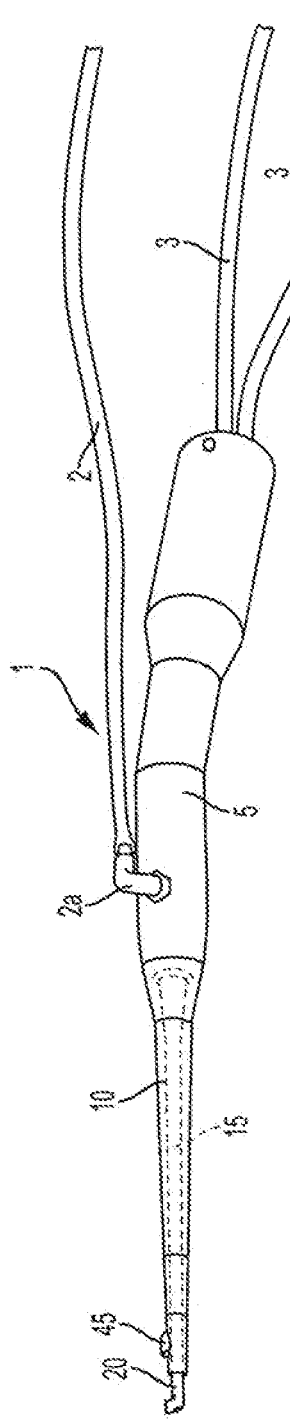
FIGS. 8A-8D are views showing an ultrasound aspirator having an integrated light according to an exemplary embodiment.
Figure 8B:
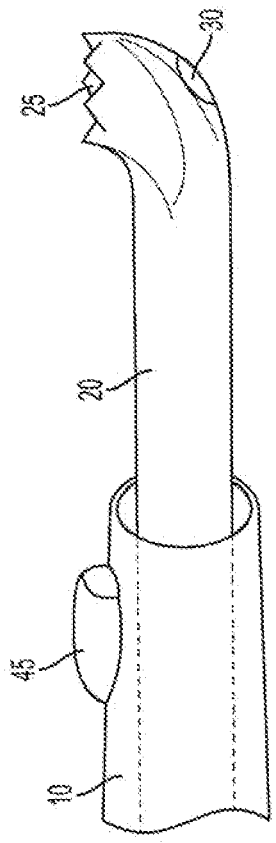
Figure 8D:
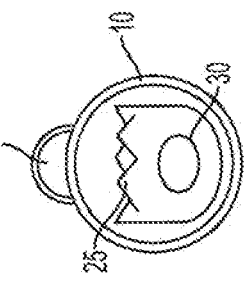
Figure 8C:
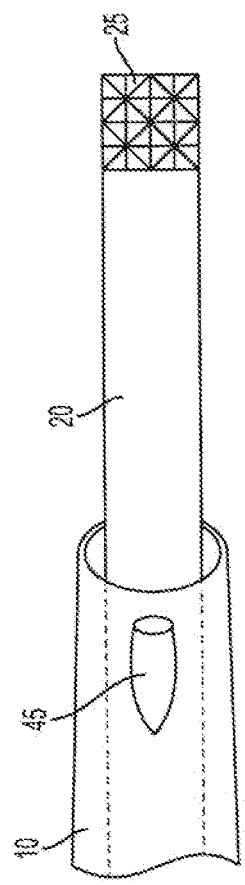

Referring to FIGS. 8A-8D, there is shown an ultrasonic aspirator 1 according to an exemplary embodiment. The ultrasonic aspirator 1 according an exemplary embodiment includes a body 5, an irrigation tube 2 connected to the body 5 via an irrigation port 2a, an aspirator wand 15 extending from the body 5, a headpiece 20 having a working surface 25, and a suction opening 30. Further, as shown in FIGS. 8B and 8C, a light 45 integrally formed with the shield 10.

It will be understood that the light 45 is not limited to being integrally formed with the shield 10. The light 45 may be provided at any location on the ultrasonic aspirator 1 to provide a user with a good visualization of the area that is targeted by the user. In this manner, a safety of the ultrasonic aspirator will be improved. According to an exemplary embodiment, light from the light 45 is directed toward the working surface 25 of the headpiece 20, as shown in FIGS. 8B-8D.

Further, the light 45 may be powered by a battery or may be connected to a constant power supply by an electrical cord. However, the light 45 is not limited to being powered in this manner, and may be powered by any means known in the art.

Referring to FIGS. 9A-9C, there is shown an ultrasonic aspirator 1 according to an exemplary embodiment. The ultrasonic aspirator 1 according an exemplary embodiment includes a body 5, an irrigation tube 2 connected to the body 5 via an irrigation port 2a, an aspirator wand 15 extending from the body 5, a headpiece 20 having a working surface 25, and a suction opening 30. Further, as shown in FIG. 9A, there is provided endoscope 50 located at an end of the body 5.

According to an exemplary embodiment, the ultrasonic aspirator 1 includes an endoscope tube 52 extending toward the headpiece 20 and terminating at the endoscope opening 53, as shown in FIGS. 9B and 9C, which is at a location proximal of the headpiece 20 to the body 5. The endoscope opening 52 is integrally formed with the shield 10. However, it will be understood that the endoscope opening 52 is not limited to being integrally formed with the shield 10. The endoscope opening 52 may be provided at any location on the ultrasonic aspirator 1 to provide a user with a good visualization of the area that is targeted by the user. In this manner, a safety of the ultrasonic aspirator will be improved.

Figure 10A:
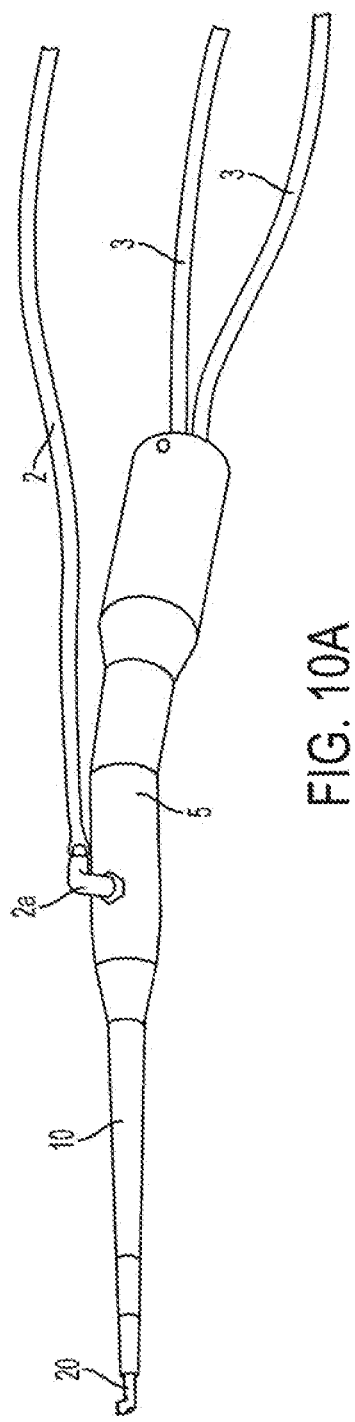
FIGS. 10A-10C are views showing an ultrasound aspirator having a suction opening on the headpiece at a location proximal to the body from a working surface of the cutting surface of the headpiece according to an exemplary embodiment.
Figure 10B:
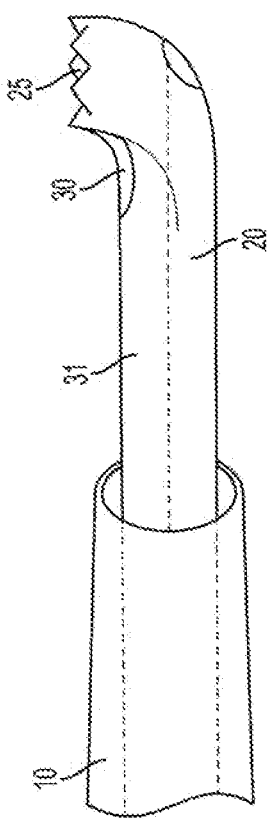
Figure 10C:
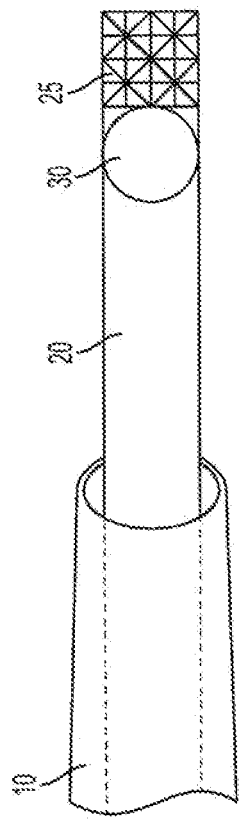

FIGS. 10A-10C show an ultrasonic aspirator according to an exemplary embodiment. The ultrasonic aspirator 1 includes a body 5, an irrigation tube 2 connected to the body 5 via an irrigation port 2a, an aspirator wand 15 extending from the body 5, and a headpiece 20 having a working surface 25.

As shown in FIGS. 10B and IC, there is provided a suction opening 30 on one side of the headpiece 20, the suction opening 30 being proximal of a distal end of the headpiece 20 and working surface 25 with respect to the body 5.

According to an exemplary embodiment, the suction opening 30 provided at the proximal location prevents damage from occurring to areas that are not targeted by the user. That is, when the working surface 25 of the headpiece 20 removes tissue or other debris, the debris is sucked through suction opening 30. In the conventional art, the suction opening 30 is provided on a distal end of the headpiece 20 and working surface 25, as shown in FIGS. 1 and 1D. In the conventional art, a user must extend the headpiece 20 toward the debris. However, this can cause unintentional contact between the headpiece 20 and objects that have not been targeted. Thus, by having the suction opening 30 provided at a position proximal of a distal end of the headpiece 20 with respect to the body 5, such unintentional contact can be avoided.

Further, although not shown, the ultrasonic aspirator 1 of FIGS. 10A-10C may include a guard 35. It will be understood that the guard could be integrally formed with the headpiece 20 or in any other manned, according to the exemplary embodiments.

Figure 11A:
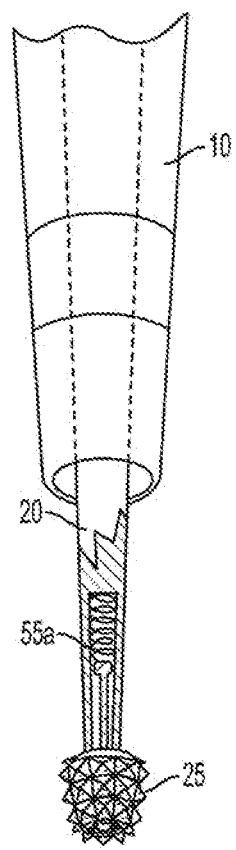
FIGS. 11A-11C are views showing an ultrasound aspirator having a sensor to determine different densities of an object according to an exemplary embodiment.
Figure 11B:
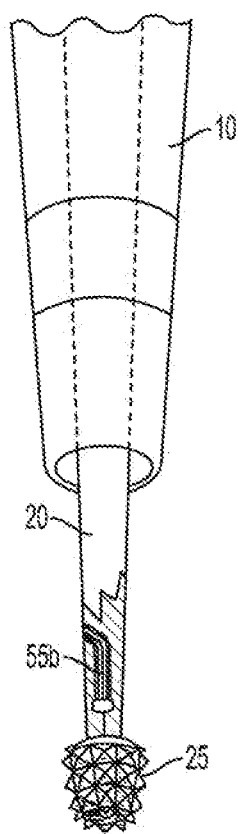
Figure 11C:
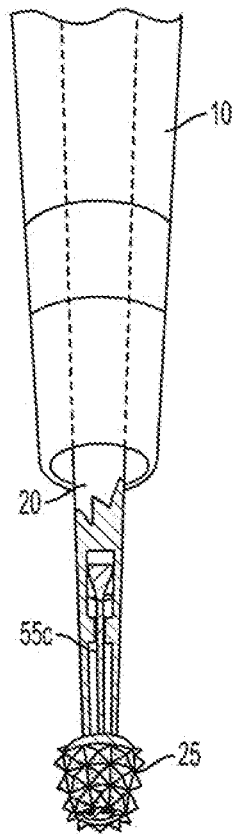

Referring to FIGS. 11A-11C, there is provided an ultrasonic aspirator 1 according to an exemplary embodiment. While not shown, it will be understood that the ultrasonic aspirator 1 may include a body 5, an irrigation tube 2 connected to the body 5 via an irrigation port 2a, and an aspirator wand 15 extending from the body 5. As shown in each of FIGS. 11A-11C, a shield 10 is provided to cover the aspirator wand 15 and a headpiece 20 having a working surface 25 extending from the shield 10.

The headpiece 20 may include a sensor to determine when the density of an object is changed. That is, a user may be using the ultrasonic aspirator in an environment having objects, such as tissues, of various densities. According to an exemplary embodiment, there is provided a pressure sensor 55sa, an ultrasound sensor 55b, or a displacement sensor 55c on the headpiece 20. The sensor determines when the density of an object which the working surface 25 is in contact with changes. Once the sensor determines that the density of the object changes, the ultrasonic aspirator may be turned off, or a mode of the ultrasonic aspirator 1 may be switched. In this manner, a user can prevent unintentionally damaging tissue surrounding the targeted tissue. It will be understood that a pressure sensor 55a, an ultrasound sensor 55b, or a displacement sensor 55c are merely exemplary embodiments, and the sensor may be any sensor known in the art to determine a change in density of an object which the working surface 25 is contacting.

Figure 12A:
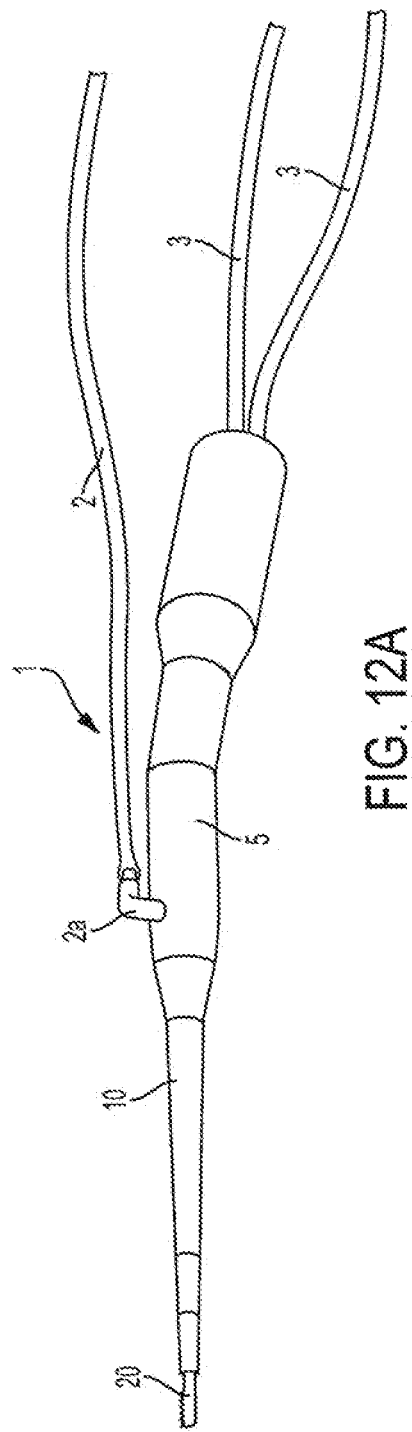
FIGS. 12A-12C are views showing a conventional ultrasound aspirator/sonicator having a specialty cutting blade projections on the headpiece.
Figure 12B:
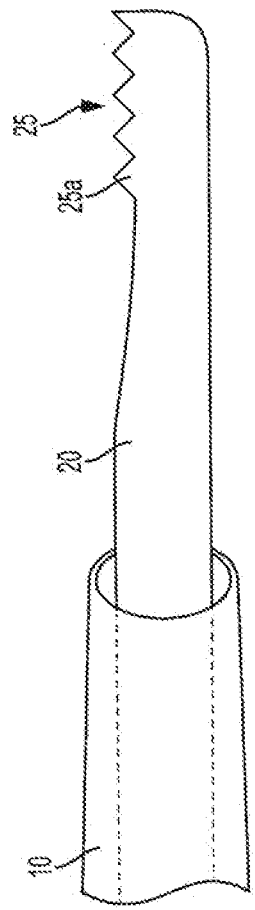
Figure 12C:
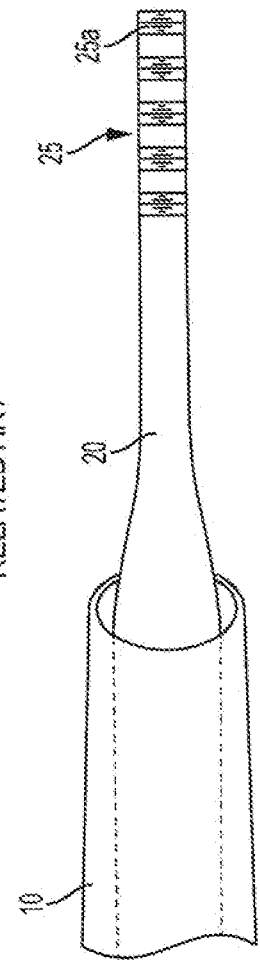

FIGS. 12A-12C are views showing a conventional ultrasonic aspirator 1 having a headpiece 20 with a working surface 25 containing projections 25a. The projections 25a allow a user to use the ultrasonic aspirator 1 as a cutting instrument in addition to using the vibration of the headpiece 20 to destroy tissue. Similar to the conventional ultrasonic aspirator 1 of FIGS. 1A-ID, the ultrasonic aspirator 1 shown in FIGS. 12A-12C includes a body 5, an aspirator wand 15 (not shown), a shield 10 covering the aspirator wand 15, and an irrigation hose connected to the body 5 via an irrigation port 2a. The headpiece 20 having the working surface 25 with projections 25a is removably attached to a distal end of the aspirator wand.

Referring to FIGS. 13A-13D, there is shown an ultrasonic aspirator 1 according to an exemplary embodiment. The ultrasonic aspirator 1 includes a body 5, an aspirator wand 15 (not shown), a shield 10 covering the aspirator wand 15, and an irrigation hose connected to the body 5 via an irrigation port 2a. A headpiece 20 having a working surface 25 with projections 25a is removably attached to a distal end of the aspirator wand 15. The projections 25a allow the use of the ultrasonic aspirator 1 in a knifelike manner to cut objects and other debris, in addition to using the vibration of the headpiece 20 to destroy tissue. As shown in FIGS. 13B-13D, the headpiece 20 includes a guard 35 integrally formed with the headpiece 20 according to an exemplary embodiment. As shown in FIG. 13B, the guard 35 extends past the headpiece 20 in a direction distal to the body 5. Thus, the guard 35 protects tissue surrounding the targeted tissue from being unintentionally destroyed while using the ultrasonic aspirator 1.

Referring to FIGS. 6A-6C, there is shown an ultrasonic aspirator 1 according to an exemplary embodiment. The ultrasonic aspirator 1 according an exemplary embodiment includes a body 5, an irrigation tube 2 connected to the body 5 via an irrigation port 2a, an aspirator wand 15 extending from the body 5, and a headpiece 20 having a working surface 25. Further, the ultrasonic aspirator 1 includes a guard 35 attached to the shield 10 and a distal end of the guard curves around a distal end of the headpiece. However, the guard 35 is not limited to being connected to the shield 10.

Figure 15A:
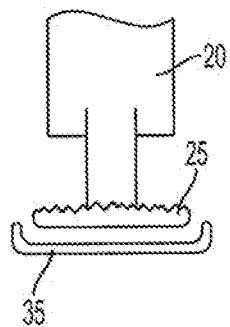
FIGS. 15A and 15B are view showing an ultrasound aspirator having a headpiece with a working surface which is curved according to an exemplary embodiment.
Figure 15B:
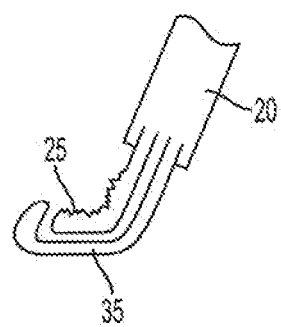

Referring to FIGS. 15A and 15B, a headpiece 20 according to an exemplary embodiment is shown. The headpiece 20 includes a working surface 25 that is curved and a guard 35 extending past the headpiece 20 in a direction distal to the body 5 and following a contour of the headpiece 20. However, exemplary embodiments are not limited to this shape.

Figure 14A:
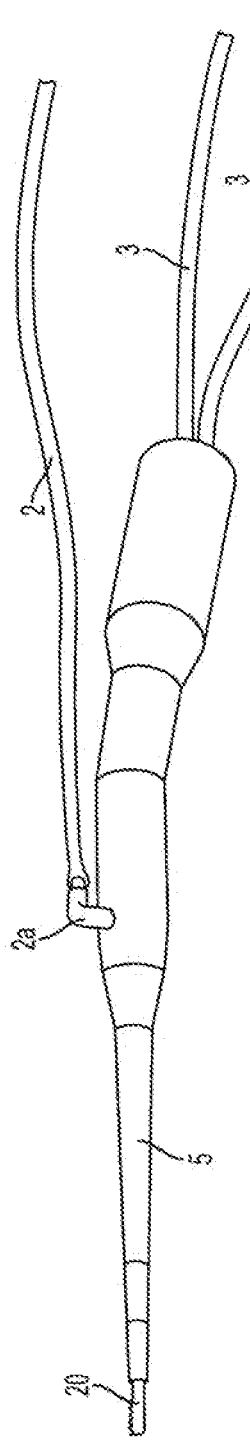
Figure 14B:
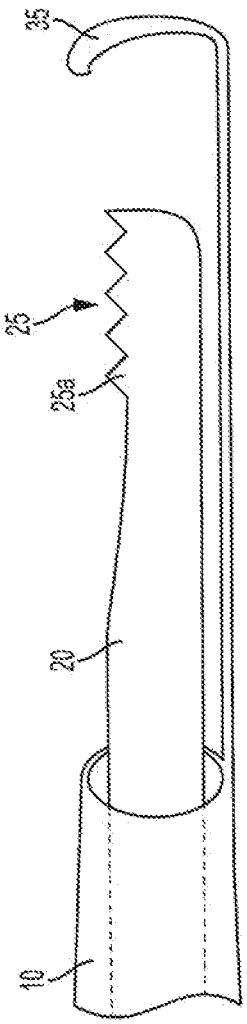
Figure 14D:
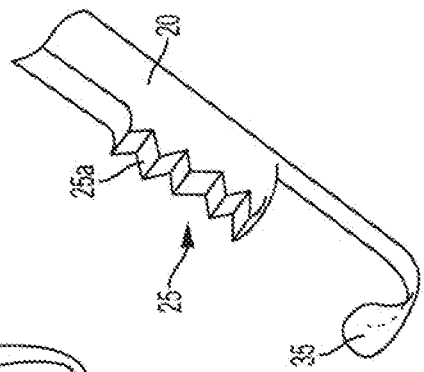
Figure 14C:
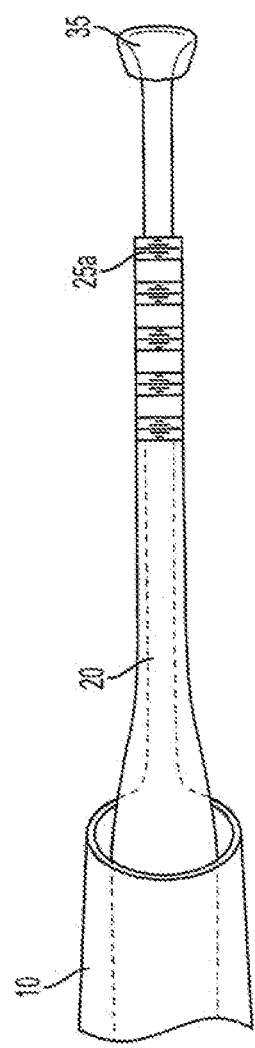

FIGS. 14A-14D show an ultrasonic aspirator 1 according to an exemplary embodiment. Similar to the embodiment shown in FIGS. 13A-13D, the ultrasonic aspirator 1 includes a body 5, an aspirator wand 15 (not shown), a shield 10 covering the aspirator wand 15, and an irrigation hose connected to the body 5 via an irrigation port 2a. A headpiece 20 having a working surface 25 with knifelike projections 25a is removably attached to a distal end of the aspirator wand 15. As shown in FIG. 14B, the guard 35 extends from the shield 10 and is separated from the headpiece 20 by a space. As shown in FIGS. 13B and 13D, the guard 35 extends past the headpiece 20 in a direction distal to the body 5 and does not contact the headpiece 20 and a distal end of the guard curves around a distal end of the headpiece past a central axis of the headpiece.

As shown in FIG. 15A, the working surface 25 of the headpiece 20 has a width greater than the width of the headpiece 20. This configuration provides a large contact surface for the working surface 25 to remove tissue. Further, the guard 35 has a same or greater width as the working surface 35a and protects tissue outside the targeted area from being contacted by the working surface 35a and a distal end of the guard curves around a distal end of the headpiece past a central axis of the headpiece.

Figure 16:
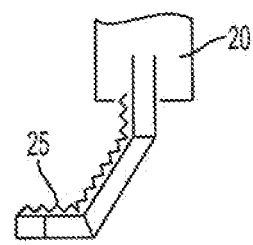
FIG. 16 is a view showing an ultrasound aspirator having a cutting surface and integrated guard that is flexible and/or jointed according to an exemplary embodiment.

FIG. 16 shows a headpiece 20 have a working surface 25 according to an exemplary embodiment. The working surface 25 is flexible to enable the headpiece 20 to access nonlinear access ports and to contact objects that are not easily accessible in an area of the body.

The working surface 25 may include hinges or may be formed of a material that is malleable along an entire surface. However, exemplary embodiments are not limited thereto. Further, the flexible area is not limited to the working surface 25, and the flexible area may include a part or the entirety of the headpiece 20. In addition, while not shown, a guard may be provided for the headpiece 20. The guard may extend past the headpiece 20 and working surface 25 in a direction distal to the body 5 and does not contact the headpiece 20 or working surface 25. Further, the guard may be rigid or may be flexible to follow the movement of the flexible working surface 25 and headpiece 20.

The flexible portion of the headpiece 20 moves according to an input by a user. While not shown, an exemplary embodiment includes handles or another input mechanism by which to manipulate the flexible portion of the headpiece 20. The headpiece 20 may be manipulated such that the headpiece 20 can be moved in a three-hundred-sixty degree rotation around an axis of the headpiece 20. In this manner, the surgeon may manipulate the headpiece 20 to access areas of the surgical area that would otherwise be difficult to access with a rigid or straight headpiece 20. It will be understood that if the ultrasonic aspirator 1 includes a guard 35, the guard 35 may bend along with the headpiece 20 or the guard 35 remain rigid with the headpiece 20 bending by the user's input and a distal end of the guard curves around a distal end of the headpiece past a central axis of the headpiece.

Referring to FIGS. 17A-17D, there is shown an ultrasonic aspirator 1 according to an exemplary embodiment. The ultrasonic aspirator 1 includes a body 5, an irrigation tube 2 connected to the body 5 via an irrigation port 2a, an aspirator wand 15 (not shown) extending from the body 5, a shield 10 covering the aspirator wand 15, and a headpiece 20 having a working surface 25. The working surface 25 of FIGS. 17B-17D include projections 25a. However, the working surface 25a is not limited thereto.

Figure 17A:
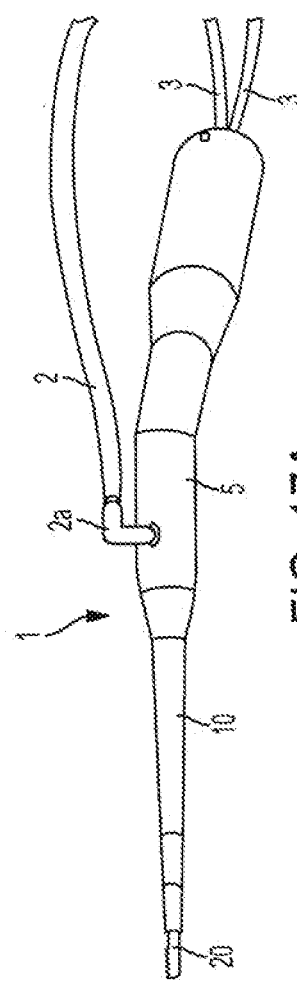
FIGS. 17A-17D are views showing an ultrasound aspirator having a guard attached to a shield with an integrated nerve stimulator/sensor on an end of the headpiece according to an exemplary embodiment.
Figure 17B:
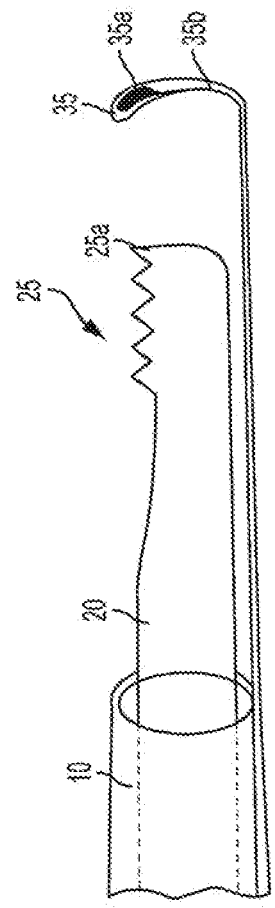
Figure 17C:
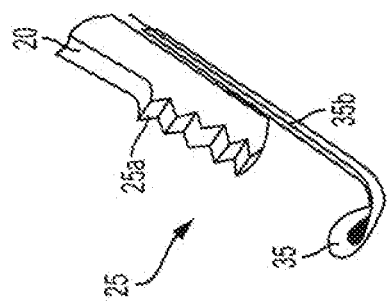
Figure 17D:
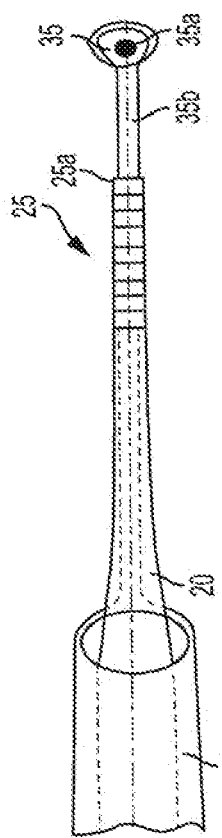

As shown in FIG. 17B, a guard 35 extends from the shield 10 to extend past the headpiece 20 and working surface 25 in a direction distal to the body 5 and does not contact the headpiece 20 or working surface 25 and a distal end of the guard curves around a distal end of the headpiece past a central axis of the headpiece. However, the guard 35 is not limited to this configuration, and may be any configuration according to the exemplary embodiments disclosed herein.

Guard 35 includes a stimulator or sensor 35a at a distal end of the guard 35 and a stimulator or sensor wire 35b extending from the stimulator 35a. The stimulator or sensor 35a receives as input a pressure, vibration, electrical or other input of adjacent structures, including an adjacent nerve, during the removal of tissue and other debris. When the stimulator/sensor 35a receives the input from an adjacent structure, a signal is sent from the stimulator 35a down the stimulator wire 35b to a user interface (not shown). In this manner, the user is made aware of an adjacent neural structure to the area that debris and tissue are being removed. This allows the user to avoid this structure, which provides an added safety measure during aspiration. In addition an electrical signal could be sent from an external source (not shown) from the stimulator wire to the stimulator which if adjacent to a neural structure could result in electrical stimulation of that structure which can be detected by sensors placed on or in skin, muscles, subcutaneous tissue or other manner known in the art in a distal area of the body enervated by that neural structure. In addition, the stimulator 35a provides additional information to a user, especially a user new to the aspiration technique, and helps prevent trauma from an unintentional contact between the headpiece 20 and the adjacent structure. Although the stimulator 35a is provided at a distal end of the guard 35, the stimulator 35a is not limited thereto, and may be provided at any location along the guard 35 to provide information of an adjacent object to the user. Further, although a stimulator wire 35b is provided to send a signal from the stimulator 35a to a user interface, exemplary embodiments are not limited thereto. The signal may be sent in any manner known in the art, including, but not limited to, using a wireless signal. This integrated nerve stimulator/sensor can be added to all shields in this application.

Figure 18A:
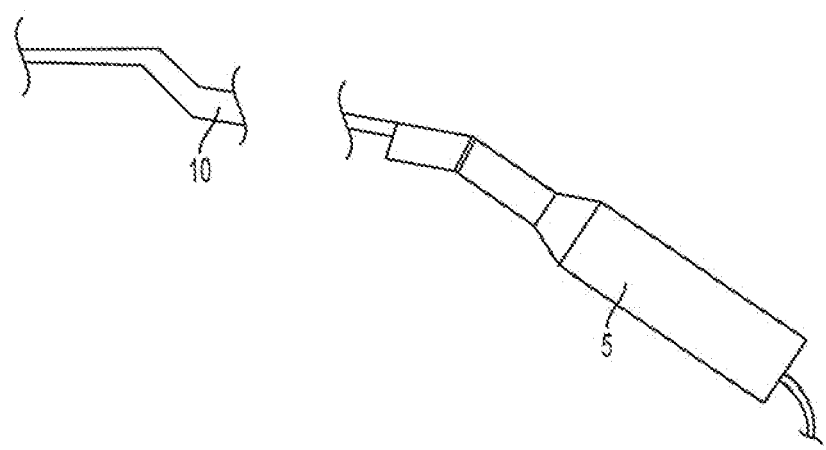
FIG. 18A shows an ultrasonic aspirator having a conventional angled body.
Figure 18B:
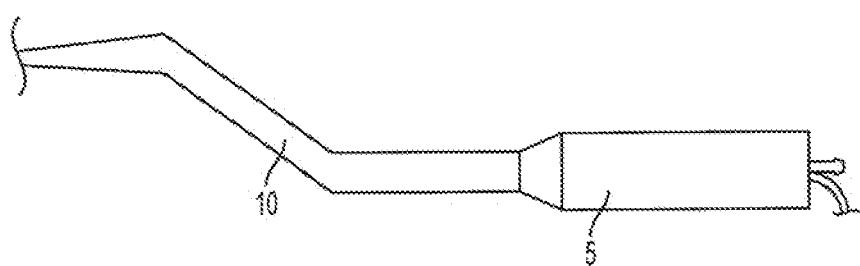
FIG. 18B shows an ultrasonic aspirator having an angled/bayoneted body and a guard for the headpiece according to an exemplary embodiment.

As shown in FIGS. 18A and 18B, there is provided a conventional ultrasonic aspirator 1 having a body 5 and a shield 10, where the body 5 is angled.

Referring to FIG. 18B, there is provided an ultrasonic aspirator 1 according to an exemplary embodiment having a body 5 and a shield 10, where the shield 10 and wand 15 are angled. According to an exemplary embodiment, the angled portion of the shield 10 and the wand 15 may be of varying length and diameter.

Figure 19:
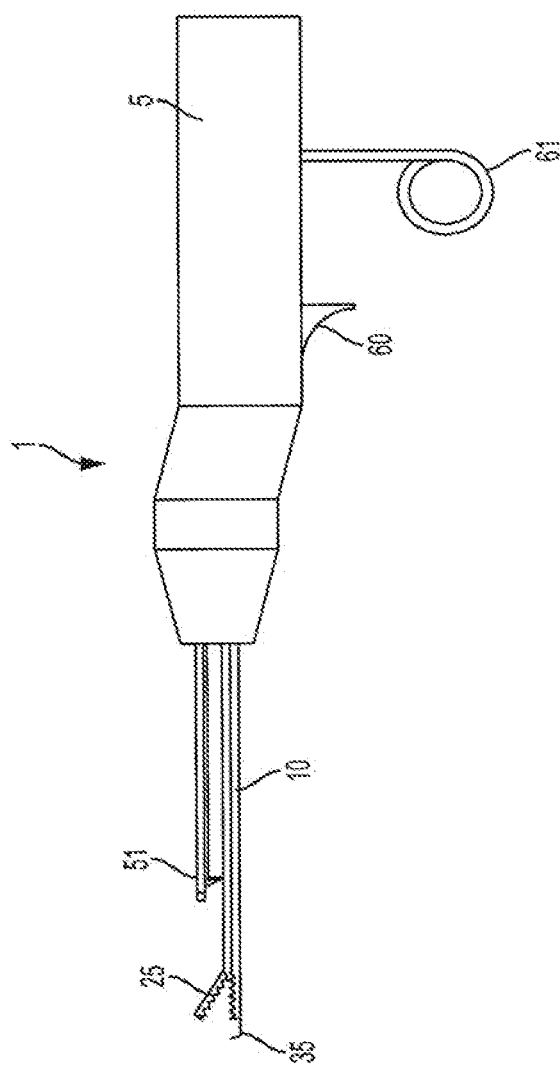
FIG. 19 shows an ultrasonic aspirator having a guard, a light, and an endoscope where the headpiece includes a grasper, according to an exemplary embodiment.

FIG. 19 shows an exemplary embodiment of an ultrasonic aspirator 1 having a working area 25 which includes a grasper. The ultrasonic aspirator 1 further includes a guard 35 extending past the headpiece 20 in a direction distal to the body 5, an endoscope 50, and a light 45. The grasper on the working area 25 is operated using the finger notch 60 and the grasper handle 61 provided on the body 5. The endoscope 50 and the light 45 provide a user with a better visualization field, which improves performance of the ultrasonic aspirator 1 and improves safety. Further, the guard 35 protects adjacent tissue from the grasper provided on the working area 25 and a distal end of the guard curves around a distal end of the headpiece past a central axis of the headpiece.

Figure 20A:
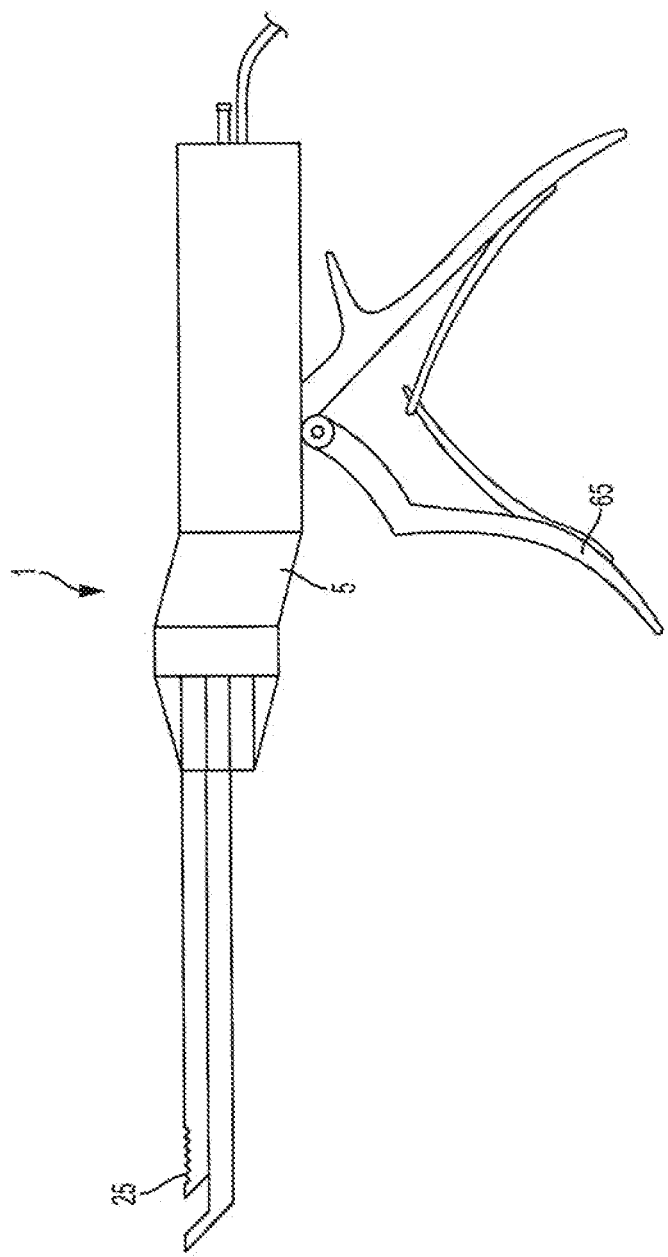
FIG. 20A shows an ultrasonic aspirator having a guard where the headpiece includes a cutting blade integrated into a biting/grasping tool, according to an exemplary embodiment.
Figure 20B:
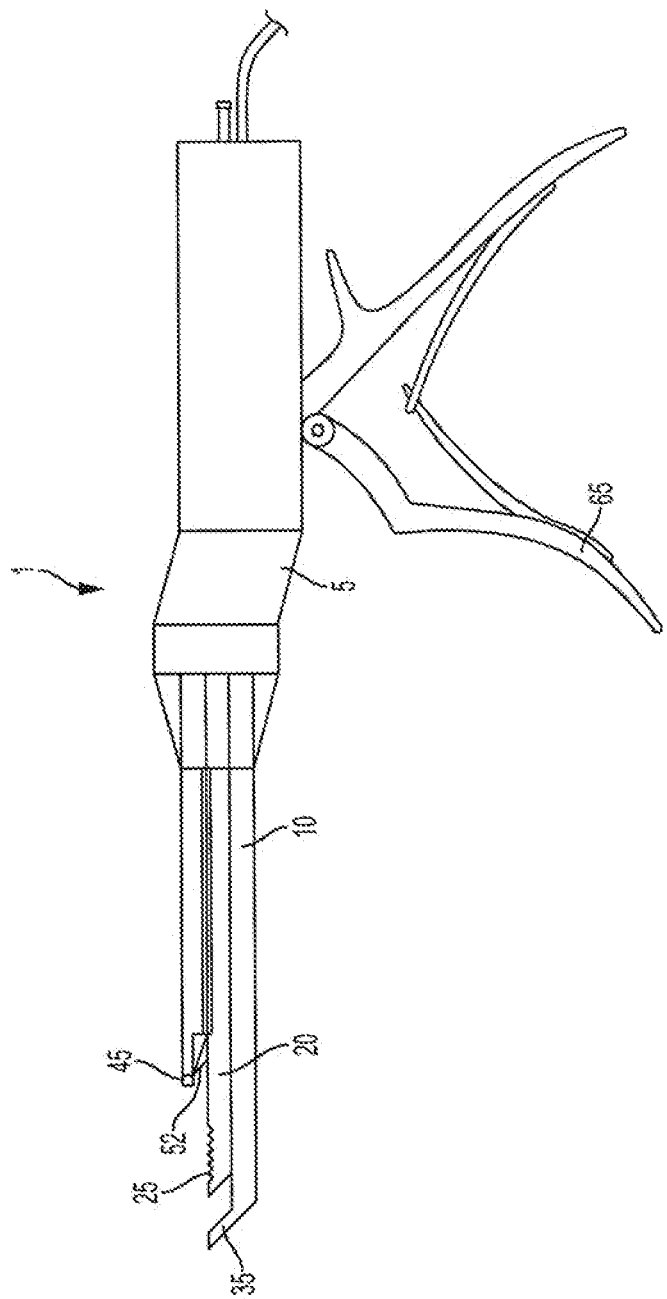
FIG. 20B shows an ultrasonic aspirator having a guard, a light, and an endoscope where the headpiece includes a cutting blade integrated into a biting/grasping tool, according to an exemplary embodiment.

FIG. 20A shows a conventional Kerrison-Ronguer action ultrasonic aspirator 1. The base 5 includes handles 65 to manipulate the working area 25. FIG. 20B shows a Kerrison-Ronguer ultrasonic aspirator 1 according to an exemplary embodiment, further including a guard 35, an endoscope 50 having an endoscope opening 52, and a light 45. The ultrasonic aspirator 1 may include one or more of the guard 35, the endoscope 50, or the light 45. Further, the guard 35 extending past the headpiece 20 in a direction distal to the body 5.

Figure 21:
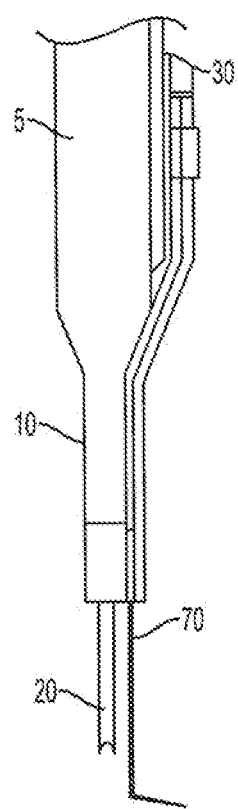
FIG. 21 shows an ultrasonic aspirator having a headpiece with a retractable reverse facing guard mechanism according to an exemplary embodiment.

Referring to FIG. 21, there is shown an ultrasonic aspirator 1 having a body 5, an irrigation hose 2 connected to the body 5, a shield 10 covering an aspirator wand (not shown), and a headpiece 20 connected to the aspirator wand. In addition, the ultrasonic aspirator 1 includes an integrated retractor 70 provided at an end of the ultrasonic aspirator 1 in a direction distal of the body 5. The retractor 70 allows the user to move structures during aspiration. According to an exemplary embodiment, the retractor 70 may be used to retract a nerve root during spinal disc removal. However, exemplary embodiments are not limited thereto.

Although exemplary embodiments of the disclosure have been shown and described, it would be appreciated by those skilled in the art that changes may be made in these exemplary embodiments without departing from the principles and spirit of the exemplary embodiments, the scope of which is defined in the claims and their equivalents.

The invention claimed is:

1. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body, wherein the guard is attached to the body and a distal end of the guard curves around a distal end of the headpiece.

2. The ultrasonic aspirator of claim 1, wherein a first side of the headpiece includes a working surface configured to aspirate an object, and wherein the first side of the headpiece further includes a suction opening in a direction proximal to the body from the headpiece.

3. The ultrasonic aspirator of claim 2, further comprising a hollow tube extending from the body through the shield and terminating at the suction opening.

4. The ultrasonic aspirator of claim 1, wherein the headpiece includes a working surface having a width greater than a width of the headpiece.

5. The ultrasonic aspirator of claim 1, wherein at least part of the headpiece is configured to bend according to a user's input.

6. The ultrasonic aspirator of claim 1, wherein the headpiece, wand and shield are bent or angled such that the ultrasonic aspirator is capable of accessing a minimally invasive tube access system.

7. The ultrasonic aspirator of claim 1, further comprising an irrigation tube connected to the body.

8. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body and a distal end of the guard curves around a distal end of the headpiece past a central axis of said headpiece, wherein the guard is integral with the headpiece.

9. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body and a distal end of the guard curves around a distal end of the headpiece, wherein the guard is separated from the headpiece by a material that is non-conductive of heat or vibration.

10. An ultrasonic aspirator, comprising:
a body;
an aspirator wand extending from the body;
a shield configured to cover the aspirator wand;
a removable headpiece removably attached to the aspirator wand;
a guard extending past an end of the headpiece in a direction distal to the body and a distal end of the guard curves around a distal end of the headpiece past a central axis of said headpiece; and
a light integrally formed at an end of the shield in a direction distal to the body.

11. An ultrasonic aspirator, comprising:
a body;
an aspirator wand extending from the body;
a shield configured to cover the aspirator wand;
a removable headpiece removably attached to the aspirator wand;
a guard extending past an end of the headpiece in a direction distal to the body and a distal end of the guard curves around a distal end of the headpiece; and
an endoscope integrally formed with the body and the shield, extending from the body to an end of the shield in a direction distal to the body.

12. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body and a distal end of the guard curves around a distal end of the headpiece past a central axis of said headpiece, wherein the headpiece includes a working surface having a plurality of protrusions configured to cut the object.

13. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body and a distal end of the guard curves around a distal end of the headpiece past a central axis of said headpiece, wherein the headpiece includes at least one joint around which a working surface of the headpiece can bend.

14. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body and a distal end of the guard curves around a distal end of the headpiece past a central axis of said headpiece, wherein the headpiece includes a sensor configured to receive an input from an adjacent object.

15. The ultrasonic aspirator of claim 14, wherein the sensor receives as input a vibration of the adjacent object.

16. The ultrasonic aspirator of claim 14, wherein the sensor is configured to determine a change in a density of an object contacted by the headpiece and wherein the aspirator is stopped when the sensor determines that the density of the object is changed.

17. The ultrasonic aspirator of claim 14, wherein the sensor is a pressure sensor.

18. The ultrasonic aspirator of claim 14, wherein the sensor is an ultrasonic sensor.

19. The ultrasonic aspirator of claim 14, wherein the sensor is a displacement sensor.

20. An ultrasonic aspirator, comprising:
a body;
an aspirator wand extending from the body;
a shield configured to cover the aspirator wand;
a removable headpiece removably attached to the aspirator wand; and
a guard extending past an end of the headpiece in a direction distal to the body and a distal end of the guard curves around a distal end of the headpiece past a central axis of said headpiece, wherein the headpiece includes a grasper at the end of the headpiece distal to the body.

* * * * *